(12) United States Patent
Ostrovsky et al.

(10) Patent No.: US 8,137,336 B2
(45) Date of Patent: Mar. 20, 2012

(54) STEERABLE MEDICAL DEVICE

(75) Inventors: Isaac Ostrovsky, Wellesley, MA (US);
Victor Shukhat, Canton, MA (US);
Jianmin Li, Lexington, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 55 days.

(21) Appl. No.: 12/490,827

(22) Filed: Jun. 24, 2009

(65) Prior Publication Data
US 2009/0326450 A1    Dec. 31, 2009

Related U.S. Application Data

(60) Provisional application No. 61/076,399, filed on Jun. 27, 2008.

(51) Int. Cl.
 A61M 25/16  (2006.01)
 A61M 25/18  (2006.01)
 A61M 37/00  (2006.01)

(52) U.S. Cl. ............... 604/533; 604/95.04; 604/539; 604/264

(58) Field of Classification Search ........... 604/95.04, 604/161, 163, 164.13, 170.03, 523, 524–529, 604/539; 600/113, 114, 101, 106, 131, 132, 600/136, 139, 153, 146–150
See application file for complete search history.

(56) References Cited

U.S. PATENT DOCUMENTS

| | | | |
|---|---|---|---|
| 4,566,437 A | 1/1986 | Yamaguchi | |
| 4,617,915 A | 10/1986 | Arakawa | |
| 4,998,916 A | 3/1991 | Hammerslag et al. | |
| 5,058,984 A | 10/1991 | Bulman et al. | |
| 5,060,660 A | 10/1991 | Gambale et al. | |
| 5,281,214 A | 1/1994 | Wilkins et al. | |
| 5,325,845 A * | 7/1994 | Adair | 600/114 |
| 5,347,989 A | 9/1994 | Monroe et al. | |
| D351,652 S | 10/1994 | Thompson et al. | |

(Continued)

FOREIGN PATENT DOCUMENTS

EP  0 521 595 B1  5/1999

(Continued)

OTHER PUBLICATIONS

International Search Report and Written Opinion for PCT/US07/11912, mailed on Sep. 12, 2008; 8 pages.

(Continued)

*Primary Examiner* — Nicholas Lucchesi
*Assistant Examiner* — Leah Stohr
(74) *Attorney, Agent, or Firm* — Finnegan, Henderson, Farabow, Garrett & Dunner (57) ABSTRACT

A steerable medical device is used to controllably introduce a guidewire or other medical instrument into a body of a patient and direct placement of the guidewire or other medical instrument in the body of the patient. The steerable medical device can include an elongated member, a steering mechanism, and an attachment member. The elongated member extends along a longitudinal axis and comprises a deflectable distal portion that is deflectable off of the longitudinal axis. The steering mechanism is adapted to control longitudinal and rotational movement of the elongated member and to control off-axis deflection of its deflectable portion. The attachment member is removably couplable to another medical device. The attachment member is moveably coupled to the steering mechanism and the elongated member.

18 Claims, 6 Drawing Sheets

U.S. PATENT DOCUMENTS

| | | |
|---|---|---|
| 5,352,237 A | 10/1994 | Rodak et al. |
| 5,413,107 A | 5/1995 | Oakley et al. |
| 5,611,777 A | 3/1997 | Bowden et al. |
| 5,656,030 A | 8/1997 | Hunjan et al. |
| 5,667,476 A | 9/1997 | Frassica et al. |
| 5,702,349 A | 12/1997 | Morizumi |
| 5,860,953 A | 1/1999 | Snoke et al. |
| 5,882,333 A | 3/1999 | Schaer et al. |
| 5,897,529 A | 4/1999 | Ponzi |
| 5,906,590 A | 5/1999 | Hunjan et al. |
| 5,957,865 A | 9/1999 | Backman et al. |
| 6,007,531 A | 12/1999 | Snoke et al. |
| 6,027,473 A | 2/2000 | Ponzi |
| 6,059,739 A | 5/2000 | Baumann |
| 6,066,125 A | 5/2000 | Webster, Jr. |
| 6,123,699 A | 9/2000 | Webster, Jr. |
| 6,171,277 B1 | 1/2001 | Ponzi |
| 6,183,435 B1 | 2/2001 | Bumbalough et al. |
| 6,183,463 B1 | 2/2001 | Webster, Jr. |
| 6,198,974 B1 | 3/2001 | Webster, Jr. |
| 6,203,507 B1 | 3/2001 | Wadsworth et al. |
| 6,267,746 B1 | 7/2001 | Bumbalough |
| 6,468,260 B1 | 10/2002 | Bumbalough et al. |
| 6,500,167 B1 | 12/2002 | Webster, Jr. |
| 6,571,131 B1 | 5/2003 | Nguyen |
| 6,605,086 B2 | 8/2003 | Hayzelden et al. |
| 6,679,873 B2 | 1/2004 | Rabiner et al. |
| 6,783,510 B1 | 8/2004 | Gibson et al. |
| 6,802,835 B2 | 10/2004 | Rabiner et al. |
| 6,837,867 B2 | 1/2005 | Kortelling |
| 6,855,137 B2 | 2/2005 | Bon |
| 6,945,956 B2 | 9/2005 | Waldhauser et al. |
| 6,966,906 B2 | 11/2005 | Brown |
| 7,037,290 B2 | 5/2006 | Gardeski et al. |
| 7,060,024 B2 | 6/2006 | Long et al. |
| 7,060,025 B2 | 6/2006 | Long et al. |
| 7,060,052 B2 | 6/2006 | Windheuser et al. |
| 7,076,285 B2 | 7/2006 | Windheuser et al. |
| 7,115,134 B2 | 10/2006 | Chambers |
| 7,232,437 B2 | 6/2007 | Berman et al. |
| 7,238,180 B2 | 7/2007 | Mester et al. |
| 7,276,062 B2 | 10/2007 | McDaniel et al. |
| 2004/0193239 A1 | 9/2004 | Falwell et al. |
| 2005/0080476 A1 | 4/2005 | Gunderson et al. |
| 2005/0125002 A1* | 6/2005 | Baran et al. .................. 606/108 |
| 2005/0256375 A1 | 11/2005 | Freed |
| 2005/0272975 A1* | 12/2005 | McWeeney et al. .......... 600/113 |
| 2005/0277874 A1 | 12/2005 | Selkee |
| 2005/0277875 A1 | 12/2005 | Selkee |
| 2005/0288627 A1 | 12/2005 | Mogul |
| 2006/0142694 A1 | 6/2006 | Bednarek et al. |
| 2006/0173448 A1 | 8/2006 | Scheller et al. |
| 2006/0252993 A1 | 11/2006 | Freed et al. |
| 2006/0264819 A1* | 11/2006 | Fischer et al. ............. 604/95.04 |
| 2007/0156116 A1 | 7/2007 | Gonzalez |
| 2007/0203474 A1 | 8/2007 | Ryan et al. |
| 2007/0270647 A1 | 11/2007 | Nahen et al. |
| 2007/0282167 A1 | 12/2007 | Barenboym et al. |
| 2008/0051802 A1 | 2/2008 | Schostek et al. |
| 2009/0171275 A1 | 7/2009 | Ostrovsky et al. |

FOREIGN PATENT DOCUMENTS

| | | |
|---|---|---|
| EP | 0 668 052 B1 | 1/2003 |
| WO | WO 93/20878 A | 10/1993 |
| WO | WO 2007/136829 A1 | 11/2007 |

OTHER PUBLICATIONS

International Preliminary Report on Patentability for PCT/US07/11912, mailed in Dec. 4, 2008; 6 pages.

International Search Report and Written Opinion for PCT/US08/86142, mailed on Mar. 11, 2009; 10 pages.

International Search Report and Written Opinion for PCT/US09/34831, mailed on May 13, 2009; 13 pages.

International Search Report and Written Opinion for PCT/US09/48792, mailed on Sep. 22, 2009; 15 pages.

* cited by examiner

STEERABLE MEDICAL DEVICE

CROSS-REFERENCE TO RELATED APPLICATIONS

This application claims priority to and the benefit of Provisional U.S. Patent Application Ser. No. 61/076,399, filed Jun. 27, 2008, the entirety of which is incorporated herein by reference.

TECHNICAL FIELD

The invention generally relates to a steerable medical device, and more particularly to a device for receiving and directing another medical instrument, such as a guidewire, to a target position in a body of a patient.

BACKGROUND INFORMATION

In some medical procedures, such as those to treat conditions in the upper urinary tract of a patient, medical instruments must be inserted into the body of the patient and positioned at a target site within the patient's body. In some procedures, an endoscope, such as a cystoscope, is first introduced into the bladder of the patient. A guidewire or another medical instrument then is introduced into the patient's body through the cystoscope. The guidewire is passed through a working channel of the cystoscope until the distal or insertion end of the guidewire exits the distal end of the cystoscope and enters the bladder of the patient. The advancing distal end of the guidewire must then somehow be directed to the target location, such as to and through the entrance of the patient's ureter. Directing the guidewire into the patient's ureter with known techniques and tools often proves difficult.

SUMMARY OF THE INVENTION

It is an object of the invention to controllably direct a guidewire or other medical instrument to a target position within a body of a patient such as a ureter of the patient. A steerable medical device according to the invention can be used to help better direct an advancing guidewire or other advancing instrument such as a stone retrieval basket, biopsy tool, laser fiber, or small catheter, for example. The device can be used with an endoscope (whether rigid, semi-rigid, or flexible) or with some other tool, particularly by passing the device through a working channel of the endoscope or other tool. Whether or not used through the working channel of an endoscope or other tool, the steerable medical device achieves easily and inexpensively the desired enhanced distal directability of an instrument that is advanced through the device. When coupled to and passed through the working channel of an endoscope or other tool, a steerable medical device according to the invention can receive a guidewire or other instrument and allow, with one-handed proximal operation, the distal manipulation required to controllably direct the distal end of the guidewire or other instrument to the desired target location within a patient's body. The steerable medical device then can be decoupled from the endoscope or other tool and removed from its working channel to leave the guidewire or other instrument at that location within the patient.

In one aspect, the invention relates to a steerable medical device comprising an elongated member, a steering mechanism, and an attachment member. The elongated member extends along a longitudinal axis. The elongated member includes a proximal end and a distal end and defines a lumen extending from the proximal end to the distal end. The elongated member includes a deflectable portion that includes the distal end and that is movable off of the longitudinal axis. The steering mechanism is adapted to control movement of the deflectable portion of the elongated member. At least a portion of the steering mechanism is fixedly coupled to at least a portion of the elongated member such that rotation of the steering mechanism in one direction about the longitudinal axis correspondingly rotates the elongated member in that one direction about the longitudinal axis. The attachment member is removably couplable to another medical device, and the elongated member and steering mechanism are movably coupled to the attachment member.

Embodiments according to this aspect of the invention can include various features. For example, the lumen of the elongated member can be accessible through an opening defined by the steering mechanism. The lumen defined by the elongated member can be a working lumen, and can be adapted to receive at least one of a guidewire, a stone retrieval basket, a biopsy tool, a laser fiber, or a catheter. The elongated member can further define a second lumen extending from the proximal end of the elongated member to the distal end of the elongated member.

The steerable medical device can also include a pull-wire coupled to the elongated member. The pull-wire can be adapted to be moved by the steering mechanism and to move the deflectable portion of the elongated member off of the longitudinal axis. The pull-wire can be disposed in the second lumen of the elongated member.

In another example, at least a portion of the deflectable portion of the elongated member can be adapted to reduce deflection resistance during movement of the deflectable portion. For example, at least a portion of the deflectable portion of the elongated member can define at least one of a recess, slot, notch, or opening adapted to reduce resistance of the elongated member during movement of the deflectable portion of the elongated member.

In another example, the proximal end of the elongated member can be fixedly coupled to a proximal end of the steering mechanism. In some embodiments, the steering mechanism also includes an actuator adapted to control movement of the deflectable portion of the elongated member. The actuator is movable between a first position and a second position and can be adapted to move the deflectable portion of the elongated member off of the longitudinal axis as the actuator is moved from its first position towards its second position. The steerable medical device can include a pull-wire extending from the steering mechanism to the distal end of the elongated member, and at least a portion of the pull-wire can be coupled to the actuator. The actuator can be disposed over a housing portion of the steering mechanism and can be movable with respect to the housing portion.

In some embodiments, the steering mechanism also includes a fastener. The fastener can have a locked position and an unlocked position. The steering mechanism and the elongated member are independently movable of the attachment member when the fastener is in its unlocked position. The attachment member can be adapted to remain substantially stationary with respect to the other medical device when the attachment member is coupled to the other medical device and the steering mechanism and elongated member are rotated in the one direction about the longitudinal axis. The attachment member can be adapted to couple the steerable medical device to a port of an endoscope.

In another example, the steerable medical device includes an indicia indicating the position of the distal end of the elongated member relative to a distal end portion of the other medical device.

In some embodiments, the steerable medical device also includes a reinforcement shaft including a proximal end and a distal end. The reinforcement shaft can be adapted to reinforce and be disposed over at least a portion of the elongated member. A portion of the reinforcement shaft can be disposable within the steering mechanism. The proximal end of the reinforcement shaft can be fixedly coupled to the steering mechanism and to the elongated member. The distal end of the reinforcement shaft can adapted to be inserted into a port of the other medical device.

In another aspect, the invention generally involves a steerable medical device that includes an elongated member, a housing, an actuator, and an attachment member. The elongated member extends along a longitudinal axis. The elongated member includes a proximal end and a distal end and defines a lumen extending from the proximal end of the elongated member to the distal end of the elongated member. The elongated member is adapted to be moved to a deflected position in which a deflectable portion of the elongated member is moved off of the longitudinal axis. The housing includes a proximal end and a distal end. The housing is fixedly coupled to the elongated member such that when the housing is moved in one rotational direction about the longitudinal axis the elongated member correspondingly rotates in the one rotational direction about the longitudinal axis. The actuator is movably coupled to the housing and is adapted to control movement of the deflectable portion of the elongated member. The attachment member is removably couplable to another medical device. The attachment member defines a proximal end and a distal end and is disposable over at least a portion of the elongated member. At least a portion of the attachment member is slidably receivable by the housing. The housing and the elongated member are independently movable of the attachment member when a position fastener disposed on the housing is unlocked.

In yet another aspect, the invention generally involves a steerable medical device that includes an elongated member, an attachment member, a reinforcement shaft, and a steering mechanism. The elongated member extends along a longitudinal axis and includes a proximal end and a distal end. The elongated member defines a lumen extending from the proximal end to the distal end. The elongated member includes a deflectable portion that includes the distal end and that is movable off of the longitudinal axis. The elongated member is adapted to be at least partially disposed in a working channel of another medical device. The attachment member is adapted to removably couple the steerable medical device to the other medical device. The attachment member defines a proximal end and a distal end, and the distal end of the attachment member is adapted to be removably coupled to a port of the other medical device. The reinforcement shaft is adapted to reinforce at least a portion of the elongated member and is disposable over at least a portion of the elongated member. The reinforcement shaft defines a proximal end and a distal end, and the distal end of the reinforcement shaft is adapted to be inserted into the port of the other medical device. The steering mechanism is adapted to control movement of the elongated member. The steering mechanism includes a housing portion fixedly coupled to at least a portion of the elongated member such that rotation of the steering mechanism in one direction about the longitudinal axis correspondingly rotates the elongated member in that one direction about the longitudinal axis. The steering mechanism include an actuator adapted to control movement of the deflectable portion off of the longitudinal axis.

BRIEF DESCRIPTION OF THE DRAWINGS

These and other features and advantages of the present invention will become better understood by reference to the following detailed description when considered in conjunction with the accompanying drawings. The drawings are for illustrative purposes only and are not necessarily to scale. Generally, emphasis is placed on conveying certain concepts and aspects according to the invention, therefore the actual dimensions of embodiments of the present invention, and their proportions to other medical instruments, may vary from the drawings.

DESCRIPTION

Apparatuses for directing the introduction and insertion of another medical instrument (such as a guidewire, stone retrieval basket, biopsy tool, laser fiber, small catheter, etc.) to a target location in a body of a patient are described herein, as are related methods. These apparatuses can be used through the working channel of an endoscope (whether rigid, semi-rigid, or flexible) or other tool. In some embodiments according to the invention, a steerable medical device is configured to be removably coupled to a rigid endoscope, some other type of endoscope (e.g., semi-rigid or flexible), or some other type of tool having a working channel and typically having some imaging capability as an endoscope usually does. A portion of the steerable medical device can be inserted into the body of the patient via the endoscope or else it can be inserted directly into the patient's body, and in any event the steerable medical device can be used to controllably introduce and direct a guidewire, or other medical instrument, into the body of the patient. The steerable medical device is adapted to direct the advancing end of the guidewire or other instrument to a target location in the body of the patient. The steerable medical device can then be uncoupled from the endoscope or other tool and removed from the patient's body while leaving the guidewire or other medical instrument in the body of the patient.

Figure 1:
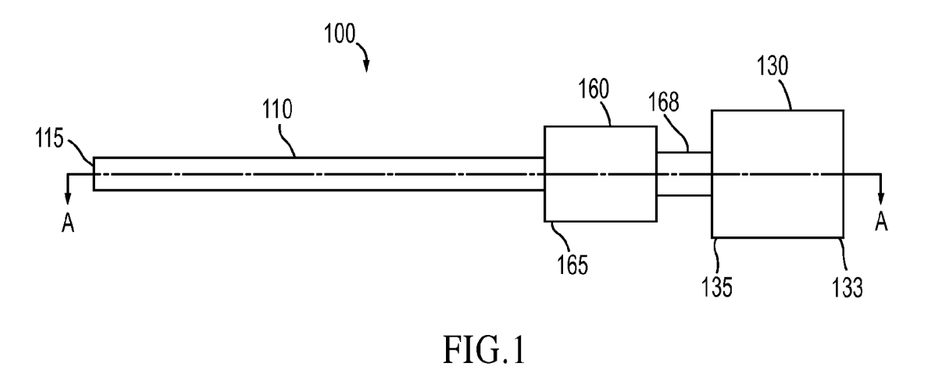
FIG. 1 is a schematic illustration of a steerable medical device according to an embodiment of the invention.
Figure 2:
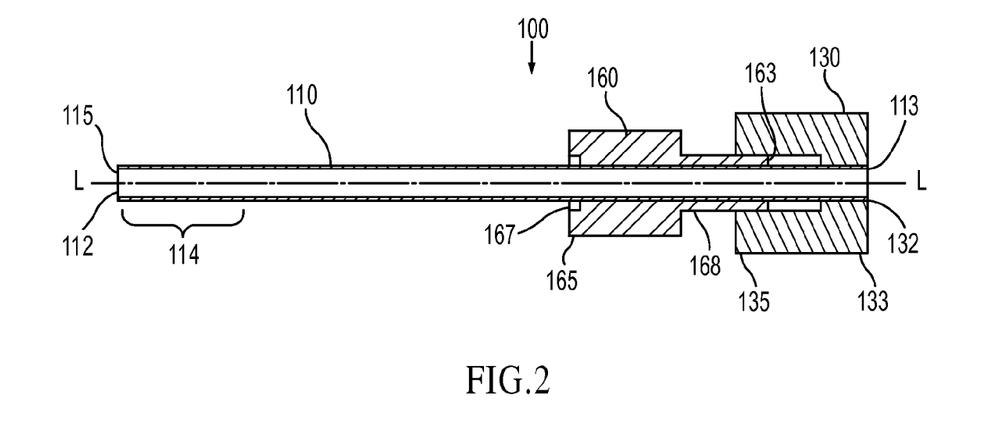
FIG. 2 is a cross-section of the steerable medical device of FIG. 1 taken along line A-A.

In one embodiment, as schematically illustrated in FIGS. 1 and 2, a steerable medical device (also referred to herein as "device") 100 includes an elongated member 110, a steering mechanism 130, and an attachment member 160. At least a portion of the device 100 can be adapted to be received by (or inserted into) a working channel of an endoscope (whether rigid, semi-rigid, or flexible) or other such tool or medical device. For example, at least a portion of the elongated member 110 can be adapted to be received by the working channel of a rigid endoscope such as a cystoscope or a laparoscope. Although the steerable medical device 100 is capable of being used on its own without passing through the working channel of some type of endoscope or other tool, it can be particularly useful when used through the working channel of an endoscope or other tool and perhaps most useful when used through the working channel of a rigid or semi-rigid endoscope.

The elongated member 110 can be tubular and includes a proximal end 113 and a distal end 115 and defines a lumen 112 extending from the proximal end to the distal end. The elongated member 110 includes a deflectable portion 114. The entirety of the elongated member 110 extends along a longitudinal axis L when the deflectable portion 114 is straight or substantially straight. The deflectable portion 114 can be deflected off of the axis L. The deflectable portion 114 includes the distal end 115 of the elongated member 110.

The steering mechanism 130 is adapted to control deflection of the deflectable portion 114 of the elongated member 110. The steering mechanism 130 is disposed at or over the proximal end 113 of the elongated member 110. The steering mechanism 130 includes a proximal end 133 and a distal end 135. The steering mechanism 130 also defines an opening or lumen 132. In some embodiments, as illustrated in FIG. 2, the lumen 132 of the steering mechanism 130 receives at least a portion of the elongated member 110 including the proximal end 113.

In some embodiments, the steering mechanism 130 is coupled to the elongated member 110. For example, as illustrated in FIG. 2, the proximal end 133 of the steering mechanism 130 is fixedly coupled (by, for example, an adhesive, an interference fit, or in some other manner) to the proximal end 113 of the elongated member 110. Because the steering mechanism 130 and the elongated member 110 are fixedly coupled, rotation of the steering mechanism in one direction (such as clockwise about the axis L) correspondingly rotates the elongated member in the same direction. Furthermore, because the steering mechanism 130 and elongated member 110 are fixedly coupled, movement of the steering mechanism 130 in a longitudinal direction (meaning in a distal or proximal direction, such as along the axis L) correspondingly moves the elongated member 110 in the same longitudinal direction.

The elongated member 110 is also referred to herein as the tubular member 110, although the shape of the elongated member 110 does not have to be cylindrical. It can have any of a variety of cross-sectional shapes instead of circular, but a circular or substantially circular cross-sectional shape for the elongated member 110 is acceptable.

The attachment member 160 is adapted to removably couple the steerable medical device 100 to an endoscope (whether rigid, semi-rigid, or flexible, but in preferred embodiments the attachment member 160 removably couples the device 100 to a rigid or semi-rigid endoscope) or other such instrument or tool with a working channel and typically some imaging capability as endoscopes usually have (not shown in FIGS. 1 and 2). For example, in some embodiments, a distal end 165 of the attachment member 160 is adapted to receive, be disposed over, or otherwise be couplable to a portion of the endoscope. In the illustrated embodiment, the distal end 165 of the attachment member 160 defines a recess 167 configured to be coupled to a portion of the endoscope. The attachment member 160 is shown disposed over a portion of the elongated member 110 that is distal to the steering mechanism 130.

The attachment member 160 is adapted to guide longitudinal movement of the steering mechanism 130 (along the axis L for example). At least a portion of the attachment member 160 is disposable within the lumen 132 of the steering mechanism 130. For example, as illustrated in FIG. 2, a guide portion 168 of the attachment member 160 is disposable within at least some of the lumen 132 of the steering mechanism 130. The steering mechanism 130 is movable with respect to the attachment member 160. For example, the steering mechanism 130 can be slidable and/or rotatable with respect to the guide portion 168 of the attachment member 160.

Referring to FIGS. 3-8 and 11-13, another embodiment of a steerable medical device 200 according to the invention is illustrated. The steerable medical device 200 is adapted to be attached to another medical device or tool, such as a rigid endoscope S, and is adapted to allow for controlled articulation of a portion of the device 200 so that another medical instrument, such as a guidewire G, can be controllably directed to a target location in a body of a patient.

Figure 3:
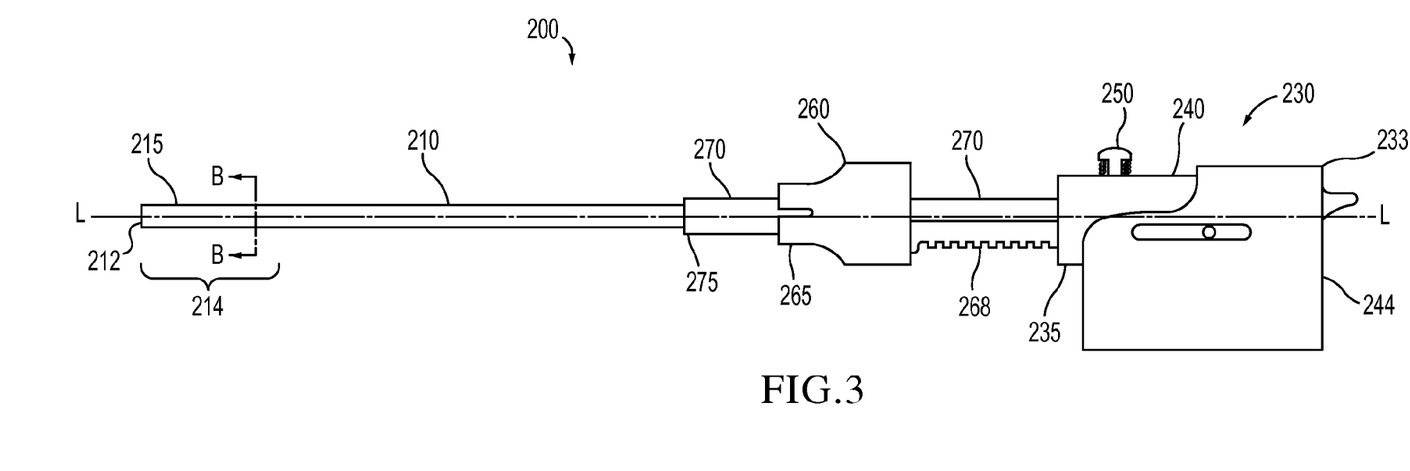
FIGS. 3 and 4 are side views of a steerable medical device according to an embodiment of the invention in a first position and a second position, respectively.

Referring to FIG. 3, the device 200 includes an elongated or tubular member 210, a steering mechanism 230, and an attachment member 260. The tubular member 210 is adapted to be inserted through a working channel of the endoscope. The steering mechanism 230 is adapted to deflect a distal portion of the tubular member 210 towards the target location in the body of the patient so that the advancing distal end of the guidewire (or other instrument) can be controllably directed or guided to the target location. The attachment member 260 is adapted to couple the device 200 to the endoscope.

Figure 11:
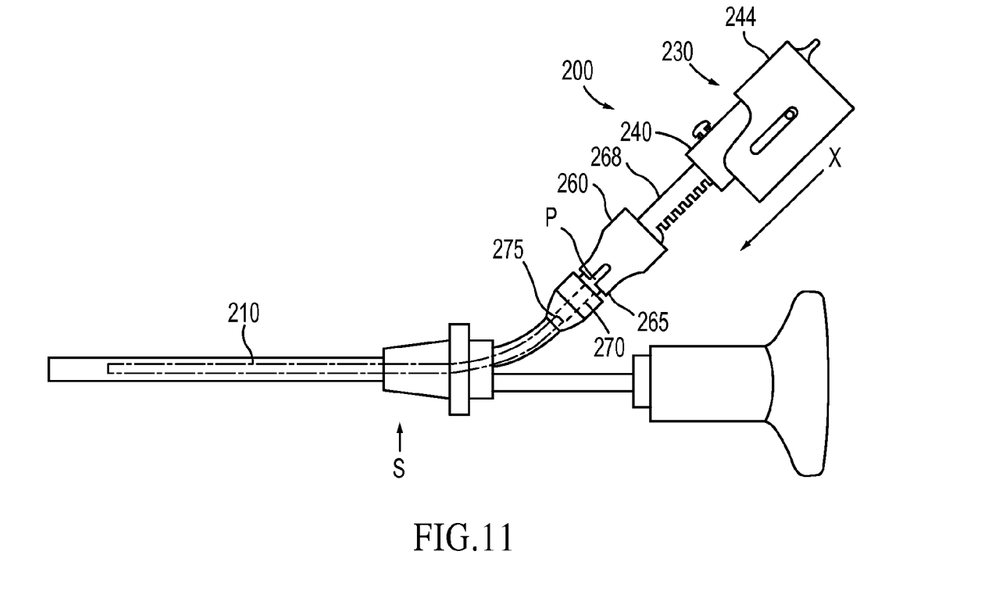
FIGS. 11-13 are side views of the steerable medical device of FIG. 3 attached to an endoscope in a first, second, and third configuration, respectively.

The tubular member 210 can be inserted into the working channel of the endoscope S through a port P of the endoscope, as illustrated in FIG. 11. The tubular member 210 is adapted to receive another medical instrument, such as a guidewire, stone retrieval basket, biopsy tool, laser fiber, or small catheter, for example. The guidewire, for example, can be inserted into the lumen 212 at the proximal end 213 of the tubular member 210. The guidewire can be passed through the lumen 212 of the tubular member 210 until a advancing (or leading) end of the guidewire extends beyond the distal end 215 of the tubular member 210.

The tubular member 210 is also adapted to be controllably articulated such that the tubular member can be used to direct the guidewire (or other instrument) to a target location in the body of the patient. At least a portion of the tubular member 210 is adapted to be deflectable, or steerable. The tubular member 210 includes a proximal end 213 and a distal end 215, and defines a lumen 212 extending between the proximal end and the distal end. The lumen 212 of the elongated member 210 can receive the guidewire (or other instrument).

The elongated member 210 includes a deflectable portion 214 that is adapted to be deflected in at least a first direction. In some embodiments, the deflectable portion 214 includes the distal end 215 of the elongated member. The deflectable portion 214 of the tubular member 210 allows an operator to target a specific location within the body of the patient. For example, the tubular member 210 of the device 200 can be inserted into a bladder of the patient through the working channel of the endoscope already positioned in the patient's bladder. The operator can then deflect the tubular member such that it approximates the entrance to the patient's ureter, or other place of treatment within the patient's bladder.

Figure 4:
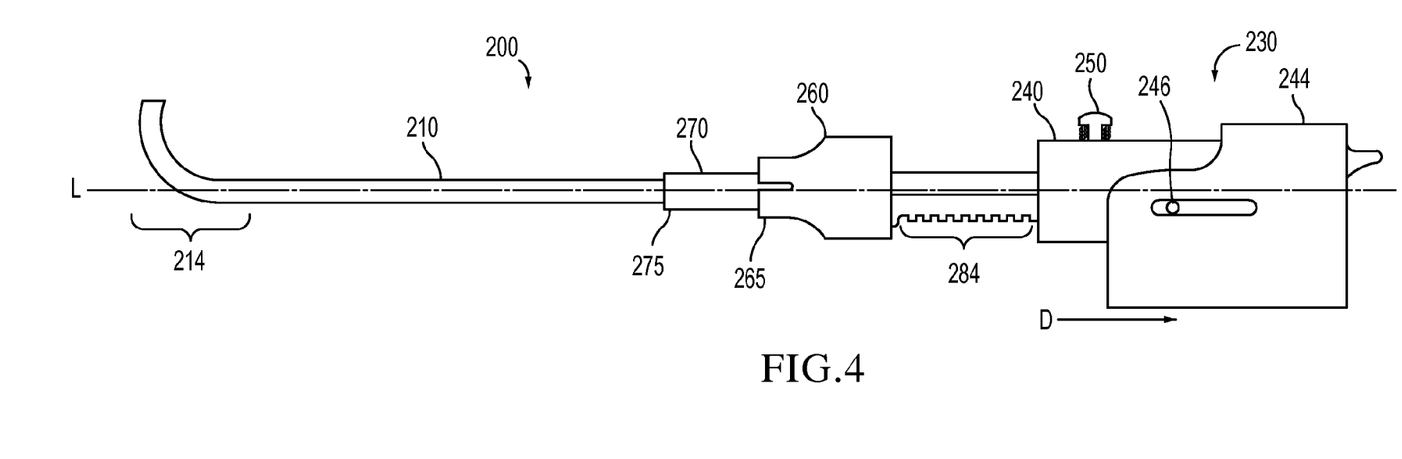
Figure 5:
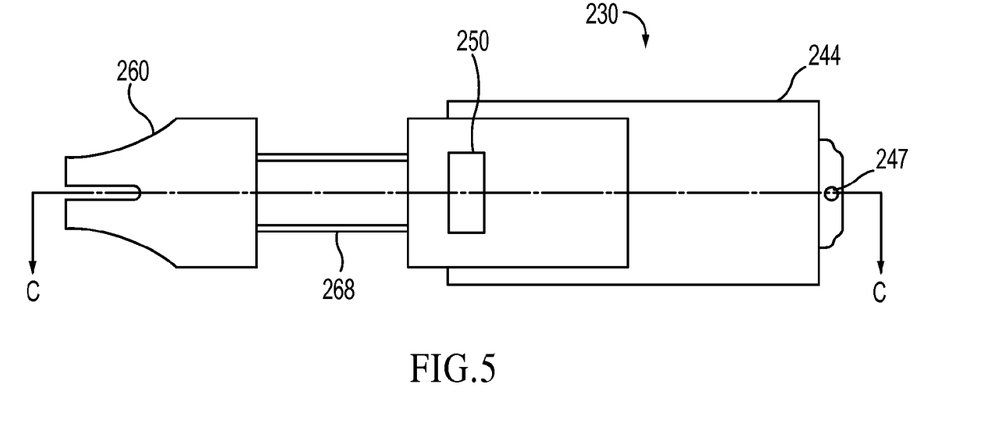
FIG. 5 is a top view of a portion of the steerable medical device of FIG. 3.

The entirety of the tubular member 210 extends along a longitudinal axis L when the deflectable portion 214 is straight or substantially straight, as illustrated in FIG. 3. The deflectable portion 214 of the tubular member 210 can be deflected in a first direction off of (or away from) the longitudinal axis L, as illustrated in FIG. 4.

Figures 9, 10:
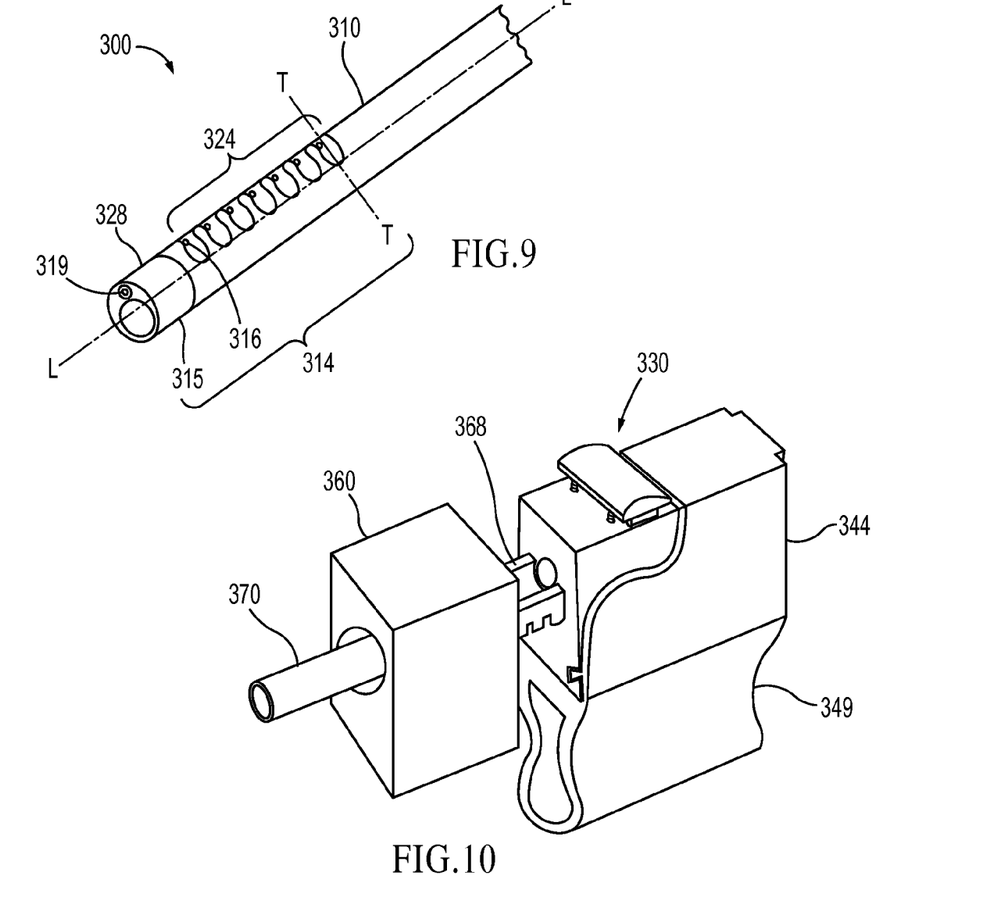
FIG. 9 is an embodiment of a portion of a steerable medical device according to an embodiment of the invention.
FIG. 10 is an embodiment of a portion of a steerable medical device according to an embodiment of the invention.

In some embodiments, the tubular member of a steerable medical device is adapted to reduce deflection resistance in the tubular member. For example, as illustrated in FIG. 9, at least a portion of a tubular member 310, such as a deflectable portion 314, defines at least one of a recess, slot, notch, or opening. The recess, slot, notch, or opening is adapted to help reduce resistance of the tubular member 310 during deflection of the distal end 315 of the tubular member. In the illustrated embodiment, for example, the deflectable portion 314 of the tubular member 310 defines a series of notches 324 (or recesses, slots, or openings). In some embodiments, each notch of the series of notches 324 extends along an axis different than the longitudinal axis L defined by the tubular member 310. In the embodiment illustrated in FIG. 9, the notches 324 extend along an axis T that is transverse to the longitudinal axis L. In other embodiments, the deflectable portion of the tubular member is constructed of a material adapted to reduce resistance to deflection, such as a material that is thinner or more flexible that the material of which the remaining portion of the tubular member is constructed.

Figure 7:
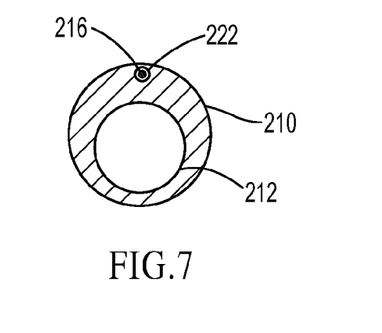
FIG. 7 is a cross-section of a portion of the steerable medical device of FIG. 3 taken along line B-B.
Figure 8:
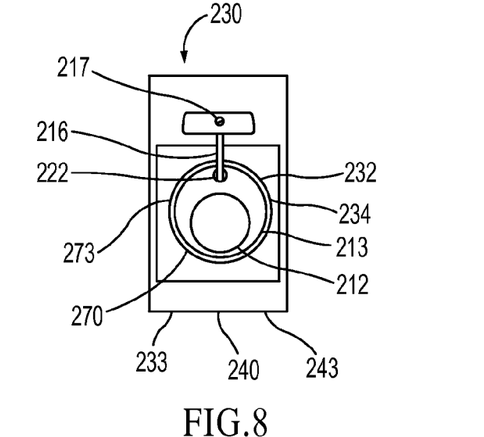
FIG. 8 is an end view of the steerable medical device of FIG. 3.

In some embodiments, as illustrated in FIGS. 7 and 8, the device 200 includes a pull-wire 216. The pull-wire 216 is adapted to be moved by the steering mechanism 230 to move the deflectable portion 214 of the tubular member 210 off of the longitudinal axis L.

In some embodiments, the lumen 212 defined by the tubular member 210 is a first (or working) lumen and the tubular member 210 further defines a second lumen 222, as illustrated in FIGS. 7 and 8. The second lumen 222 extends from the proximal end 213 of the tubular member 210 to the distal end 215 of the tubular member. The first and second lumens 212, 222 can have varying cross-sectional shapes and/or diameters. For example, the working lumen 212 can be larger than the second 222 lumen. In another example, the working lumen can have a circular cross-sectional shape and the second lumen can have a different cross-sectional shape, such as hexagonal, oval, or square.

The pull-wire 216 can be disposed within the second lumen 222. The pull-wire 216 defines a proximal end 217 and a distal end (not shown in FIGS. 3-8). The proximal end 217 of the pull-wire 216 is coupled to the steering mechanism 230, as illustrated in FIG. 8. The distal end of the pull-wire 216 is coupled to the distal end 215 of the tubular member 210. In some embodiments, as illustrated in FIG. 9, an attachment ring 328 is disposed on the distal end 315 of the tubular member 310. The distal end 319 of the pull-wire 316 is coupled to the attachment ring 328.

The tubular member can be constructed of any suitable material. For example, the tubular member can be constructed of a biocompatible polymeric material or a thermoplastic elastomer. In another example, the tubular member defining the first and second lumens can be constructed from a Pebax® extrusion.

The tubular member can be constructed of a flexible, semi-rigid, or rigid material. If the tubular member is constructed of a more rigid material, such as Teflon® or nylon, it is beneficial for the deflectable portion of the tubular member to be adapted to decrease deflection resistance, such as by having a series of notches as described above.

Referring to FIGS. 3-8, the steering mechanism 230 of the device 200 is adapted to control movement of the deflectable portion 214 of the tubular member 210. The steering mechanism 230 is adapted to be controlled by a single hand of an operator. For example, a physician can control movement of the steering mechanism 230 with one hand while using the other hand to control a guidewire being inserted into the body of the patient through the tubular member 210.

The steering mechanism 230 includes a proximal end 233 and a distal end 235. In some embodiments, the steering mechanism 230 is disposed at or over the proximal end 213 of the tubular member 210. At least a portion of the steering mechanism 230 is fixedly coupled to at least a portion of the tubular member 210. For example, the proximal end 233 of the steering mechanism 230 can be fixedly coupled to the proximal end 213 of the tubular member 210. The steering mechanism 230 and tubular member 210 are fixedly coupled such that rotation of the steering mechanism in one direction about the longitudinal axis L correspondingly rotates the elongated member in that one direction about the longitudinal axis. Similarly, movement of the steering mechanism in one longitudinal direction (such as in a proximal or distal direction along the longitudinal axis L) correspondingly moves the elongated member in that one longitudinal direction.

In some embodiments, at least a portion of the steering mechanism 230 defines an opening or lumen 232, as illustrated in FIG. 8. The lumen 232 of the steering mechanism 230 is adapted to receive at least a portion of the tubular member 210. In the illustrated embodiment, the lumen 232 of the steering mechanism 230 receives (or is disposed over) the proximal end 213 of the tubular member 210.

In some embodiments, the steering mechanism 230 includes an actuator 244 and a housing 240 (also referred to herein as "housing portion"). In the illustrated embodiment, the actuator 244 is disposed over a portion of the housing 240 of the steering mechanism 230. The actuator 244 is movable with respect to the housing 240, as described in more detail herein.

The actuator 244 is adapted to control movement of the deflectable portion 214 of the tubular member 210 off of the longitudinal axis L. For example, the actuator 244 can be used to direct or control deflection of the deflectable portion 214 of the tubular member 210.

As illustrated in FIGS. 3 and 4, the actuator 244 is movable, with respect to the housing 240, between a first position (FIG. 3) and a second position (FIG. 4). When the actuator 244 is in its first position, the tubular member 210 extends along the longitudinal axis L (or is straight). The actuator 244 is adapted to move the deflectable portion 214 of the tubular member 210 away from the longitudinal axis L as the actuator is moved from its first position towards its second position. In some embodiments, the actuator 244 is moved to its second position by sliding the actuator in the direction of arrow D, as illustrated in FIG. 4. When the actuator 244 is in its second position, the deflectable portion 214 of the tubular member 210 is off of the longitudinal axis L.

In some embodiments, the steering mechanism is adapted to limit movement of the actuator. For example, in the illustrated embodiment, a protrusion 246 on the housing 240 is adapted to limit the sliding movement of the actuator 244.

As illustrated in FIG. 10, in some embodiments, an actuator 344 of a steering mechanism 330 includes a portion 349 adapted to be more easily gripped, grasped, or pulled by an operator. For example, the actuator 344 can include a contoured portion 349 adapted to be gripped by an operator. In other embodiments, the portion can have a different configuration adapted to allow the user to more easily control actuation of the actuator.

Although the actuator 244 is illustrated as being a slidable actuator disposed over a portion of the housing 240 of the steering mechanism 230, in other embodiments, the actuator has a different configuration. For example, the actuator can be a slide, button, lever, or another type of actuator disposed on the steering mechanism.

In some embodiments, at least a portion of the pull-wire 216 is coupled to the actuator 244. For example, as illustrated in FIG. 8, the proximal end 217 of the pull-wire 216 is coupled to the actuator 244 of the steering mechanism 230. In the illustrated embodiment, the pull-wire 216 extends through an opening 247 (illustrated in FIGS. 5 and 6) defined by a portion of the actuator 244. As the actuator 244 is moved towards its second position, the actuator moves (or pulls on) the pull-wire 216 causing the pull-wire to deflect the deflectable portion 214 of the tubular member 210.

Although the device 200 is illustrated and described as including a single pull-wire 216 and as including a tubular member 210 movable in one direction off of the longitudinal axis L, in other embodiments, the device can include more than one pull-wire and the tubular member can be movable in more than one direction off of the longitudinal axis L. For example, in one embodiment, the device includes a tubular member that includes a deflectable portion that is moveable in one direction, such as to the right from the perspective of the operator, and another direction different than the one direction, such as to the left from the perspective of the operator. In another embodiment, the deflectable portion of the tubular member is moveable (or deflectable) 360 degrees about the longitudinal axis L. In some embodiments, the device includes two, three, four, or more pull-wires adapted to move the tubular member off of the longitudinal axis L. In some embodiments, the tubular member defines more than two lumens. For example, the tubular member can define four lumens, such as to accommodate four pull-wires.

The housing 240 of the steering mechanism 230 includes a proximal end 243 and a distal end 245. In some embodiments, the housing 240 defines the opening or lumen 232 of the steering mechanism 230. For example, in some embodiments, the lumen 232 extends from a proximal opening 234 at the proximal end 243 of the housing 240 to a distal opening 236 at the distal end 245 of the housing.

The proximal end 213 of the tubular member 210 is disposed in (or received in) the lumen 232 of the housing 240. The lumen 212 of the tubular member 210 is accessible through the proximal opening 243 of the housing 240. For example, a guidewire, stone retrieval basket, biopsy tool, laser fiber, small catheter, or another medical instrument can be inserted into the lumen 212 of the tubular member 210 through the proximal opening 243 of the housing 240.

In some embodiments, the housing 240 is the portion of the steering mechanism 230 fixedly coupled to the tubular member 210. For example, the proximal end 243 of the housing 240 can be fixedly coupled to the proximal end 213 of the tubular member 210. Because the housing 240 and tubular member 210 are fixedly coupled, when the housing of the steering mechanism 230 is rotated in one direction about the longitudinal axis L, the tubular member correspondingly moves or rotates in that one direction about the longitudinal axis L. Similarly, when the housing 240 of the steering mechanism 230 is moved in one longitudinal direction, for example in a distal direction along the longitudinal axis L, the tubular member correspondingly moves in that one longitudinal direction.

Figure 6:
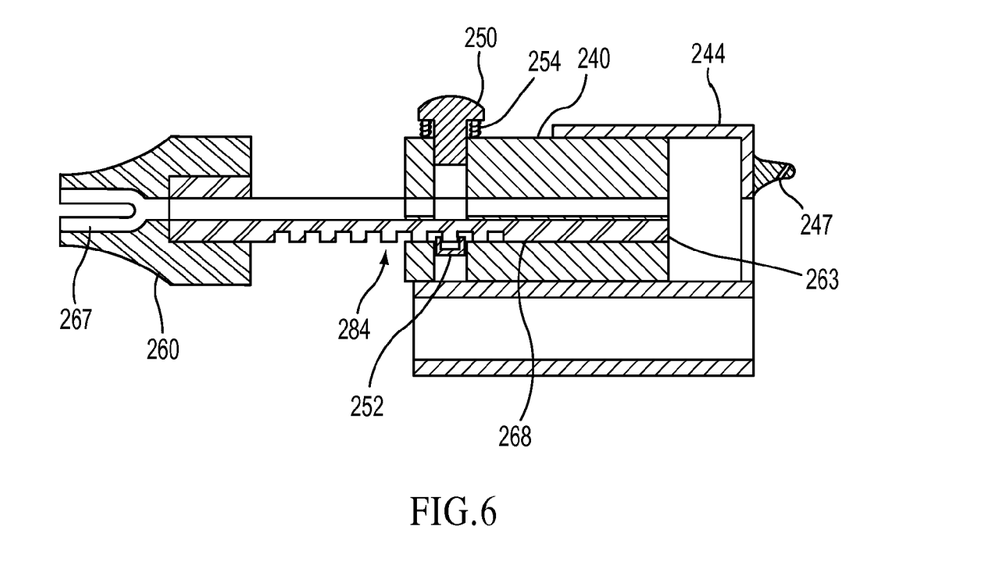
FIG. 6 is a cross-section of the portion of the steerable medical device of FIG. 5 taken along line C-C.

In some embodiments, the steering mechanism 230 of the device 200 further includes a fastener 250 (also referred to herein as a "position fastener"). The fastener 250 is adapted to fix the position of the steering mechanism 230, and thus the tubular member 210, with respect to the attachment member 260. The fastener 250 has an unlocked position and a locked position. When the fastener 250 is in the unlocked position, the steering mechanism 230 and tubular member 210 are independently movable of the attachment member 260. When the fastener 250 is in its locked position, as illustrated in FIG. 6, the steering mechanism 230 and tubular member 210 are fixed with respect to (or are not independently movable of) the attachment member 260.

The fastener 250 is biased towards its locked position, such as via springs 254. When the fastener 250 is locked, a portion 252 of the fastener engages a portion of the attachment member 260. In the embodiment illustrated in FIG. 6, a portion 252 of the fastener 250 is engaged with or overlays one of a series of teeth 284. To move the tubular member 210 with respect to the attachment member 260, the fastener 250 is pushed downwards towards the housing 240 and the portion 252 of the fastener disengages the tooth.

The fastener 250 allows an operator to selectively longitudinally position the tubular member 210, such as to achieve a certain depth in the body of the patient or extension of the tubular member 210 beyond a distal end of the endoscope or to accommodate variations in lengths of various endoscopes or distal optics equipment, and then fasten or fix the tubular member with respect to the attachment member 260 to prevent further longitudinal movement.

The attachment member 260 of the steerable medical device 200 is adapted to removably couple the device to the endoscope. For example, the attachment member 260 is adapted to removably couple the device 200 to the port of the endoscope. By being removable, the steerable medical device 200 can be coupled to (or attached to) the endoscope and then be removed from the endoscope at the operator's discretion.

When the attachment member 260 is coupled to the endoscope, the attachment member remains substantially stationary with respect to the endoscope when the steering mechanism 230 and the tubular member 210 are moved in at least one of a rotational direction about the longitudinal axis L or a longitudinal direction along the longitudinal axis.

In some embodiments, the distal end 265 of the attachment member 260 is adapted removably couple to the endoscope. For example, as illustrated in FIG. 6, the distal end 265 of the attachment member 260 defines a recessed portion 267 adapted to be coupled to or disposed over a portion of the endoscope. In some embodiments, the distal end 265 of the attachment member 260 is adapted to snap onto the port of the endoscope. In other embodiments, the attachment member 260 is coupled to the endoscope using another known coupling means, including an adhesive, an interference fit, or interlocking recesses, among others.

Once the attachment member 260 of the device 200 is coupled to the endoscope, the operator need not continue to manually support the device because the coupling of the attachment member to the endoscope will support the device. Thus, the operator is able to use one hand to control the actuator 244 of the steering mechanism 230 and the other hand to manipulate the guidewire, or other medical instrument, being inserted into the working channel of the endoscope and into the body of the patient.

The steering mechanism 230 and the tubular member 210 are movably coupled to the attachment member 260. As illustrated in FIGS. 3 and 4, the attachment member 260 can be disposed over and movable with respect to at least a portion of the tubular member 210 distal to the portion of the tubular member over which the steering mechanism 230 is disposed. Thus, when the attachment member 260 is coupled to the endoscope, the steering mechanism 230 and tubular member 210 can be moved with respect to the attachment member. For example, the steering mechanism 230 and tubular member 210 can be slidably movable with respect to the attachment member 260 in a longitudinal direction. In another example, the steering mechanism 230 and tubular member 210 can be rotatably movable with respect to the attachment member 260. The attachment member is adapted to remain substantially stationary with respect to the other medical device when the attachment member is coupled to the endoscope and the steering mechanism and tubular member are moved longitudinally in a direction along the longitudinal axis and/or rotationally about the longitudinal axis. Because the steering mechanism 230 and tubular member 210 are movable with respect to the attachment member 260, the steering mechanism and tubular member can be moved in any longitudinal or rotational direction when the attachment member is coupled to the endoscope, thus allowing for controllable placement of the distal end 215 of the tubular member within the body of a patient.

The attachment member 260 is configured to guide longitudinal movement of the steering mechanism 230 and tubular member 210, for example in at least one of a proximal or a distal direction along the longitudinal axis L. In some embodiments, at least a portion of the attachment member 260 is received within the steering mechanism 230, such as within an opening or lumen 232 of the steering mechanism. For example, a guide portion 268 of the attachment member 260, which includes the proximal end portion 263 (illustrated in FIG. 6) of the attachment member 260, can be disposed within the lumen 232 of the steering mechanism 230. The steering mechanism 230 is movable over the guide portion 268 of the attachment member 260 received or disposed in the steering mechanism. In some embodiments, the guide portion 268 (or axial guide) of the attachment member 260 defines a lumen or recess adapted to receive at least a portion of the tubular member 210. For example, as illustrated in FIG. 10, the guide portion 268 can have a semi-circular cross-section, and thus define a recess (the "U" of the semi-circle) adapted to receive a portion of the tubular member. The tubular member 210 is also movable with respect to the guide portion 268 of the attachment member 260.

In some embodiments, the steerable medical device 200 includes an indicia of the longitudinal position of the distal end 215 of the tubular member 210. For example, the indicia can indicate a depth of insertion of the tubular member 210 into the body of the patient by corresponding to a length of extension of the distal end 215 of the tubular member 210 beyond a distal end of the endoscope. For example, as illustrated in FIGS. 4 and 6, the device 200 includes an indicia that is a series of protrusions or teeth 248. Each protrusion (or tooth) corresponds to a measurement of the depth extension of the tubular member 210 beyond the distal end of the endoscope and into the body of the patient.

In the illustrated embodiment, the indicia 284, the series of teeth 284 that engage the fastener 250, and the guide 268 are the same piece of the device 200 having multiple functions. In other embodiments, however, the indicia is different than the teeth configured to engage the fastener and/or the guide. For example, the indicia can be included on or disposed elsewhere on the device 200. In other embodiments, for example, the device can include an index or position indexer upon which the indicia is disposed, and the index or position indexer can be coupled to at least one of the steering mechanism, tubular member, or the attachment member. Although the indicia is illustrated as a series of protrusions, in other embodiments, the indicia can be one or a series of lines, ridges, numbers, colors, or any other visual or tactile indicia corresponding to a depth of insertion of the tubular member.

In some embodiments, as illustrated in FIGS. 3 and 4, the steerable medical device 200 includes a reinforcement (or stiffener) shaft 270. The reinforcement shaft 270 is adapted to reinforce at least a portion of the tubular member 210. For example, the reinforcement shaft 270 provides reinforcement or support to the portion of the tubular member 210 that is inserted into the port of the endoscope. The reinforcement shaft 270 includes a proximal end 273 and a distal end 275 and defines a lumen (not shown) extending from the proximal end to the distal end of the reinforcement shaft.

The reinforcement shaft 270 is disposable over at least a portion of the tubular member 210. For example, the lumen of the reinforcement shaft 270 is adapted to receive a portion of the tubular member 210. In some embodiments, as illustrated in FIG. 8, a portion, such as the proximal end 273, of the reinforcement shaft 270 is disposed within the lumen 232 of the steering mechanism 230. In some embodiments, the proximal end 273 of the reinforcement shaft 270 is coupled to the proximal end 233 of the steering mechanism 230 and to the proximal end 213 of the tubular member 210. In some embodiments, the reinforcement shaft 270, tubular member 210, and steering mechanism 230 are fixedly coupled together such that when one is rotated or moved longitudinally about or along the longitudinal axis L, each of the others is correspondingly rotated or moved longitudinally about or along the longitudinal axis L. In other embodiments, as illustrated in FIG. 10, a reinforcement shaft 370 does not extend into the steering mechanism 330, but only reinforces the portion of the tubular member (not shown) extending through the attachment member 360 and entering into the port of the endoscope.

A portion of the reinforcement shaft 270 is adapted to be inserted into the endoscope. In some embodiments, the distal end 275 of the reinforcement shaft 270 is adapted to be inserted into, or extend telescopically into, the endoscope, such as into the port P of the endoscope S, as illustrated in dashed lines in FIG. 11.

A steerable medical device according to the invention can be used to perform or assist in a variety of medical procedures. For example, the steerable device 200 can be used in procedures to treat conditions in the upper urinary tract of a patient, such as kidney stones, or in the bladder of a patient, such as tumors. Referring to FIGS. 11 through 14, a medical device, such as endoscope S, is inserted into the patient's body. For example, in some procedures, the endoscope is inserted into a bladder of the patient. The tubular (or elongated) member 210 of the steerable medical device 200 (shown in dashed lines in FIG. 11) is at least partially inserted into the working channel of the endoscope S through port P.

Figure 12:
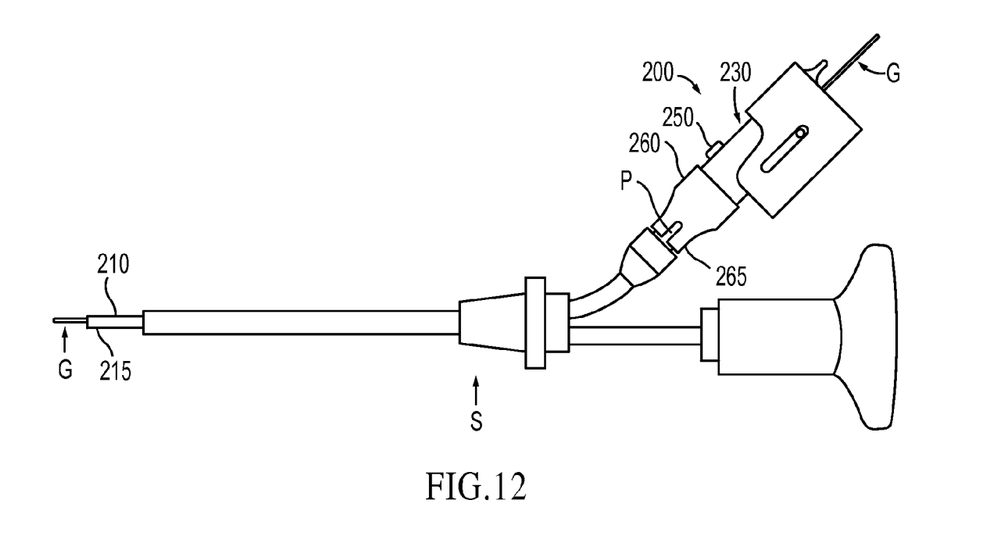

The attachment member 260 of the device 200 removably couples the device to the endoscope S. As illustrated in FIG. 12, the fastener 250 of the steering mechanism 230 is moved from its locked to its unlocked position and the steering mechanism 230 is moved in a distal direction (indicated by the arrow X in FIG. 11) with respect to the attachment member 260. Movement of the steering mechanism 230 distally when the fastener 250 is unlocked advances the tubular member 210 until its distal end 215 extends beyond a distal end of the endoscope S. The steering mechanism 230, and thus the tubular member 210, can be alternatively moved distally and proximally until the operator achieves a desired extension of the distal end 215 of the tubular member 210 beyond the distal end of the endoscope S.

A guidewire G is inserted into the working lumen 212 of the tubular member 210 via the proximal opening of the steering mechanism 230. The guidewire G is passed through the lumen 212 of the tubular member 210 until a distal end of the guidewire is at or near the distal end 215 of the tubular member.

Figure 13:
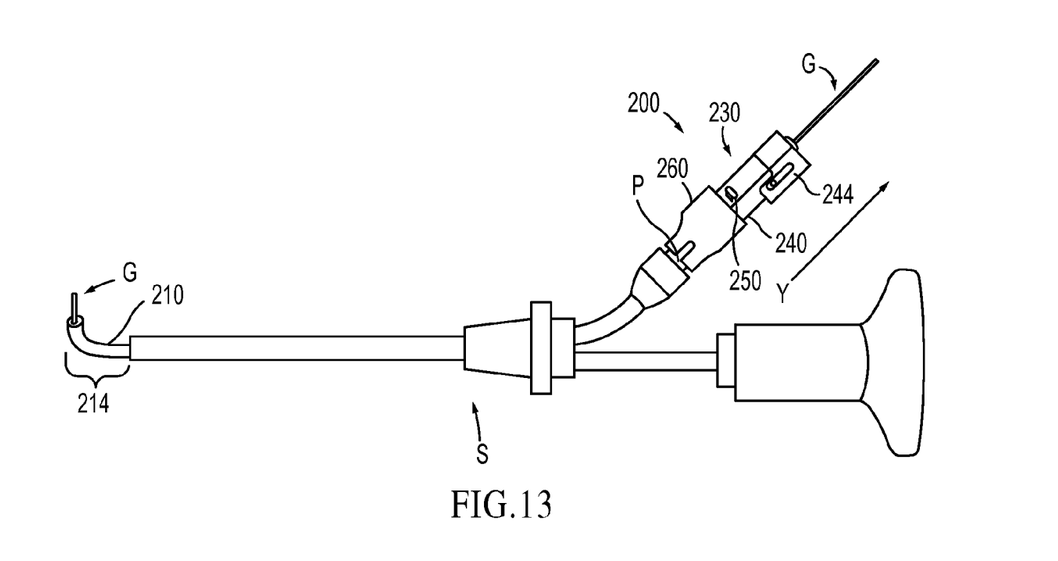

Referring to FIG. 13, the actuator 244 of the steering mechanism 230 is moved in the direction of arrow Y to its second position, and the deflectable portion 214 of the tubular member 210 is moved away from the longitudinal axis. The actuator 244 moves a pull wire (not shown in FIG. 13) to deflect the deflectable portion 214 of the tubular member 210 off of the longitudinal axis. The steering mechanism 230 is partially rotated in one direction with respect to the attachment member 260 (and the longitudinal axis) towards the handle of the scope (i.e., in a counterclockwise direction), and therefore the tubular member 210 is partially rotated in the one direction. The steering mechanism and tubular member can be rotated in clockwise and counterclockwise directions until the deflected distal end of the tubular member faces or approximates the target location of the body of the patient. If necessary, the tubular member can be readjusted in a proximal or distal direction to better approximate the deflected distal end of the tubular member to the target location of the patient's body.

The ability to control deflection, rotation, and longitudinal position of the tubular member allows the physician (or other operator) to introduce the guidewire G, or other medical instrument, to a target location within the body of the patient. For example, the physician can manipulate the tubular member 210 until the guidewire G is positioned at the entrance to the patient's ureter. Furthermore, the physician can control the deflection, rotation, and longitudinal position of the tubular member with one hand, leaving the other hand free to manipulate the guidewire.

Figure 14:
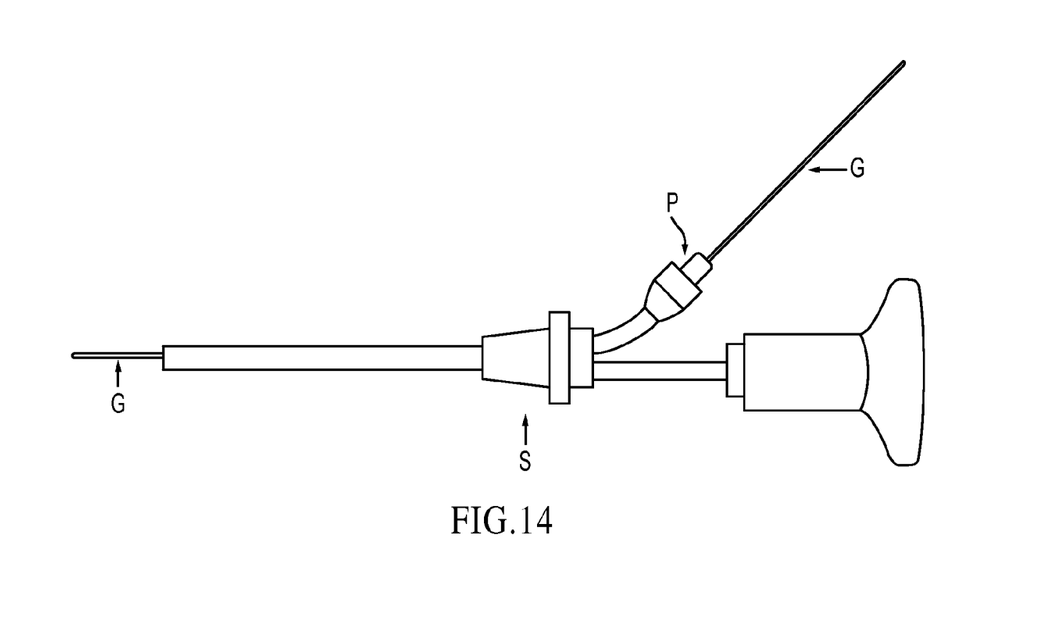
FIG. 14 is a side view of the endoscope of FIGS. 11-13 with the steerable medical device removed.

With the guidewire G positioned at the target location, the attachment member 260 is decoupled (or removed) from the port P and the steerable medical device 200 is removed in the direction of arrow Y, as indicated in FIG. 13, from the body of the patient and from the endoscope S while leaving the guidewire G substantially in position at the target location in the body of the patient. The device 200 can be removed over the guidewire G or other medical device, leaving the guidewire G or other medical device available in the endoscope S for further treatment procedures, as illustrated in FIG. 14.

Although use of the steerable medical device in a medical procedure has been illustrated and described herein as occurring in one order, in other procedures the steps can occur in a different order. For example, the steering mechanism 230 and tubular member 210 can be longitudinally and/or rotationally positioned before the distal end 215 of the tubular member is deflected.

Additionally, although the steerable medical device has been illustrated and described herein mostly as being used in conjunction with another medical device (such as a rigid endoscope) and through a working channel of that other device, a steerable medical device according to the invention can be used to controllably direct a guidewire or other instrument without passing through the working channel of another device.

In some embodiments, the steerable medical device 200 is a guiding catheter adapted to be disposable after a single-use. After the operator has used the guiding catheter to position the guidewire, or other medical instrument, in the body of the patient, the operator can remove the guiding catheter from the body of the patient and discard it.

While various embodiments of the invention have been described above, it should be understood that they have been presented by way of example only and are not limiting on the invention. The breadth and scope of the invention should not be limited by any of the above-described embodiments.

What is claimed is:

1. A steerable medical device, comprising:
an elongated member extending along a longitudinal axis and including a proximal end and a distal end and defining a lumen extending from the proximal end to the distal end, the elongated member comprising a deflectable portion that includes the distal end and that is movable off of the longitudinal axis;
a steering mechanism adapted to control movement of the deflectable portion of the elongated member, at least a portion of the steering mechanism fixedly coupled to at least a portion of the elongated member such that rotation of the steering mechanism in one direction about the longitudinal axis correspondingly rotates the elongated member in that one direction about the longitudinal axis; and
an attachment member removably couplable to another medical device, the elongated member and steering mechanism movably coupled to the attachment member; and wherein the steering mechanism includes a fastener, the fastener having a locked position and an unlocked position, the steering mechanism and the elongated member independently movable of the attachment member when the fastener is in its unlocked position;
and wherein the elongated member is configured to be longitudinally slidable through the attachment member.

2. The steerable medical device of claim 1, wherein the lumen of the elongated member is accessible through an opening defined by the steering mechanism.

3. The steerable medical device of claim 1, wherein the lumen defined by the elongated member is adapted to receive at least one of a guidewire, a stone retrieval basket, a biopsy tool, a laser fiber, or a catheter.

4. The steerable medical device of claim 1, further comprising: a pull-wire coupled to the elongated member, the pull-wire adapted to be moved by the steering mechanism and to move the deflectable portion of the elongated member off of the longitudinal axis.

5. The steerable medical device of claim 4, wherein the lumen defined by the elongated member is a working lumen, the elongated member further defining a second lumen extending from the proximal end of the elongated member to the distal end of the elongated member, the pull-wire disposed in the second lumen of the elongated member.

6. The steerable medical device of claim 1, wherein at least a portion of the deflectable portion of the elongated member is adapted to reduce deflection resistance during movement of the deflectable portion.

7. The steerable medical device of claim 1, wherein at least a portion of the deflectable portion of the elongated member defines at least one of a recess, slot, notch, or opening, the at least one recess, slot, notch or opening adapted to reduce resistance of the elongated member during movement of the deflectable portion of the elongated member.

8. The steerable medical device of claim 1, wherein the proximal end of the elongated member is fixedly coupled to a proximal end of the steering mechanism.

9. The steerable medical device of claim 1, wherein the steering mechanism further comprises an actuator movable between a first position and a second position, the actuator adapted to move the deflectable portion of the elongated member off of the longitudinal axis as the actuator is moved from its first position towards its second position.

10. The steerable medical device of claim 1, wherein the steering mechanism further comprises an actuator adapted to control movement of the deflectable portion of the elongated member, the steerable medical device further comprising:
a pull-wire extending from the steering mechanism to the distal end of the elongated member, at least a portion of the pull-wire is coupled to the actuator.

11. The steerable medical device of claim 1, wherein the steering mechanism further comprises an actuator adapted to control movement of the deflectable portion of the elongated member, the actuator is disposed over a housing portion of the steering mechanism, the actuator movable with respect to the housing portion.

12. The steerable medical device of claim 1, wherein the attachment member is adapted to remain substantially stationary with respect to the other medical device when the attachment member is coupled to the other medical device and the steering mechanism and elongated member are rotated in the one direction about the longitudinal axis.

13. The steerable medical device of claim 1, wherein the attachment member is adapted to couple the steerable medical device to a port of an endoscope.

14. The steerable medical device of claim 1, further comprising an indicia indicating the position of the distal end of the elongated member relative to a distal end portion of the other medical device.

15. The steerable medical device of claim 1, further comprising a reinforcement shaft including a proximal end and a distal end, the reinforcement shaft adapted to reinforce and be disposed over at least a portion of the elongated member.

16. The steerable medical device of claim 15, wherein a portion of the reinforcement shaft is disposable within the steering mechanism, the proximal end of the reinforcement shaft fixedly coupled to the steering mechanism and to the elongated member.

17. The steerable medical device of claim 15, wherein the distal end of the reinforcement shaft is adapted to be inserted into a port of the other medical device.

18. A steerable medical device, comprising:
an elongated member extending along a longitudinal axis and including a proximal end and a distal end and defining a lumen extending from the proximal end of the elongated member to the distal end of the elongated member, the elongated member adapted to be moved to a deflected position in which a deflectable portion of the elongated member is moved off of the longitudinal axis;
a housing including a proximal end and a distal end, the housing fixedly coupled to the elongated member such that when the housing is moved in one rotational direction about the longitudinal axis the elongated member correspondingly rotates in the one rotational direction about the longitudinal axis;
an actuator movably coupled to the housing; the actuator adapted to control movement of the deflectable portion of the elongated member; and
an attachment member removably couplable to another medical device, the attachment member defining a proximal end and a distal end and being disposable over at least a portion of the elongated member, at least a portion of the attachment member slidably receivable by the housing, the housing and the elongated member being independently movable of the attachment member in a longitudinal direction when a position fastener disposed on the housing is unlocked.

* * * * *

UNITED STATES PATENT AND TRADEMARK OFFICE
CERTIFICATE OF CORRECTION

PATENT NO. : 8,137,336 B2
APPLICATION NO. : 12/490827
DATED : March 20, 2012
INVENTOR(S) : Isaac Ostrovsky et al.

It is certified that error appears in the above-identified patent and that said Letters Patent is hereby corrected as shown below:

Claim 18, col. 16 lines 31-34, should read, --the housing, the housing and the elongated member being independently movable of the attachment member when a position fastener disposed on the housing is unlocked; and wherein the elongated member is configured to be longitudinally slidable through the attachment member.--

Signed and Sealed this
Fifth Day of June, 2012

David J. Kappos
*Director of the United States Patent and Trademark Office*